(12) United States Patent
Wu

(10) Patent No.: US 6,998,262 B2
(45) Date of Patent: Feb. 14, 2006

(54) **POLYSACCHARIDE EXTRACT OF *DIOSCOREA* SP. AND AN ORALLY ACTIVE PHARMACEUTICAL COMPOSITION COMPRISING THE SAME**

(75) Inventor: Rong-Tsun Wu, Taipei (TW)

(73) Assignee: National Yang-Ming University, Taipei (TW)

(*) Notice: Subject to any disclaimer, the term of this patent is extended or adjusted under 35 U.S.C. 154(b) by 291 days.

(21) Appl. No.: 10/160,670

(22) Filed: May 30, 2002

(65) Prior Publication Data

US 2003/0224066 A1   Dec. 4, 2003

(51) Int. Cl.
*C08B 37/00* (2006.01)
*C12P 19/04* (2006.01)

(52) U.S. Cl. .......................... 435/274; 435/72; 435/99; 435/101

(58) Field of Classification Search ................ 435/274, 435/72, 99, 101
See application file for complete search history.

(56) References Cited

U.S. PATENT DOCUMENTS 5,118,673 A * 6/1992 Carpenter et al. ............. 514/54

OTHER PUBLICATIONS

Tomoda et al, Chem. Pharm. Bull. 29(11):3256-3261 (1981).*
Sefa-Dedeh et al, Cereal Chem. 54(4):746-759 (1977).*
Lin et al., J. Food Sci. 33:599-606 (1968).*
J.L. Beneytout et al., *Biochemical and Biophysical Research Communications*, 207(1): 398-404, 1995.
Mohsen Araghiniknam et al., *Life Sciences*, 59(11): 147-157, 1996.
Hiroshi Hikino et al., *Planta Medical*, (3): 168-171, 1986.
*J. of China Pharma. Univ.*, 25(6): 369-372, 1994.
Hang Yue Yu, *J. Plant Resour. & Environ.*, 5(2): 5-8, 1996.
*Henan TCM*, 16(6):349-350, 1996.
*Henan TCM*, 12(1): 23-24, 1992.

* cited by examiner

*Primary Examiner*—Francisco Prats
(74) *Attorney, Agent, or Firm*—Morgan&Finnegan, LLP

(57) ABSTRACT

This invention provides a *Dioscorea* polysaccharide extract prepared by the method of this invention, which enhances the immunological activities by regulating the gene expression of cytokines. This invention further provides a *Dioscorea* polysaccharide extract, which has a synergistic effect with an oral vaccine and is capable of eliminating oral tolerance.

5 Claims, 11 Drawing Sheets

(A)

(B)

(A)

(B)

(A) Intestinal IgA (B) Pulmonary IgA (A)

(B)

(A)

(B)

SEQUENCE LISTING

<160> NUMBER OF SEQ ID NOS: 12

<210> SEQ ID NO 1
<211> LENGTH: 25

-continued

<212> TYPE: DNA
<213> ORGANISM: Homo sapiens

<400> SEQUENCE: 1
atggacactc ttcctgaact cacct                                    25

<210> SEQ ID NO 2
<211> LENGTH: 26
<212> TYPE: DNA
<213> ORGANISM: Homo sapiens

<400> SEQUENCE: 2
caggacaggt atagattctt tcctttt                                  26

<210> SEQ ID NO 3
<211> LENGTH: 23
<212> TYPE: DNA
<213> ORGANISM: Homo sapiens

<400> SEQUENCE: 3
atgggtctca acccccagct agt                                      23

<210> SEQ ID NO 4
<211> LENGTH: 24
<212> TYPE: DNA
<213> ORGANISM: Homo sapiens

<400> SEQUENCE: 4
gctctttagg ctttccagga agtc                                     24

<210> SEQ ID NO 5
<211> LENGTH: 24
<212> TYPE: DNA
<213> ORGANISM: Homo sapiens

<400> SEQUENCE: 5
atgaagttcc tctctgcaag agac                                     24

<210> SEQ ID NO 6
<211> LENGTH: 24
<212> TYPE: DNA
<213> ORGANISM: Homo sapiens

<400> SEQUENCE: 6
cactaggttt gccgagtaga tctc                                     24

<210> SEQ ID NO 7
<211> LENGTH: 24
<212> TYPE: DNA
<213> ORGANISM: Homo sapiens

<400> SEQUENCE: 7
tgaacggtac acactgcatc ttgg                                     24

<210> SEQ ID NO 8
<211> LENGTH: 23
<212> TYPE: DNA
<213> ORGANISM: Homo sapiens

<400> SEQUENCE: 8
cgactccttt tccgcttcct gag                                      23

<210> SEQ ID NO 9

```
<211> LENGTH: 41
<212> TYPE: DNA
<213> ORGANISM: Homo sapiens

<400> SEQUENCE: 9
tggaccgcaa caacgccatc tatgccatct atgagaaaac c                          41

<210> SEQ ID NO 10
<211> LENGTH: 32
<212> TYPE: DNA
<213> ORGANISM: Homo sapiens

<400> SEQUENCE: 10
tggagctgaa gcaatagttg gtatccaggg ct                                    32

<210> SEQ ID NO 11
<211> LENGTH: 20
<212> TYPE: DNA
<213> ORGANISM: Homo sapiens

<400> SEQUENCE: 11
gactacctca tgaagatcct                                                  20

<210> SEQ ID NO 12
<211> LENGTH: 20
<212> TYPE: DNA
<213> ORGANISM: Homo sapiens

<400> SEQUENCE: 12
ccacatctgc tggaaggtgg                                                  20
```

POLYSACCHARIDE EXTRACT OF DIOSCOREA SP. AND AN ORALLY ACTIVE PHARMACEUTICAL COMPOSITION COMPRISING THE SAME

FIELD OF THE INVENTION

The present invention relates to an oral composition comprising a polysaccharide extract of *Dioscorea* sp. prepared by the method of this invention which can be used to enhance the immunity, and relates to an oral composition comprising a polysaccharide extract of *Dioscorea* sp. capable of enhancing the systemic and mucosal immune responses of a subject upon vaccination with an oral vaccine.

BACKGROUND OF THE INVENTION

*Dioscorea*, also known as "wild yam," is a member of the monocotyledonous family Dioscoreaceae, which is distributed in the tropical and subtropical regions. There are about 650 species in the world, of which 93 species and 9 varieties are found in China, and 14 species and 5 varieties are found in Taiwan. *Dioscorea* is one of the very important pharmaceutical plants used in the traditional Chinese medicine. In the Chinese pharmacopoeia, the medicinal uses of *Dioscorea* rhizome are prescribed for indigestion, anorexia, diarrhea and diabetes. *Dioscorea* sp. has many superior characteristics in the rhizome such as high viscosity and high contents of viscous polysaccharide comprising carbohydrate, mannose, arabinose, glucose, galactose, xylose, and rhamnose, starch, protein, vitamins and minerals. It also contains dioscin, diosgenin, phytic acid, allantoin, dopamine, batatasin, dioscorea-mucilage B, and sterols. Certain studies indicate that the unit structure of polysaccharide prepared from *Dioscorea batatas* is $\beta$-(1→4)-linked D-mannose residues containing C-3 branch chain, and the average molecular weight of polysaccharide obtained from *Dioscorea japonica* is about 81,000.

*Dioscorea* has been studied for years for their medicinal effects. For example, in Biochemical & Biophysical Research Communications 207(1): 398–404, 1995 February, J. L. Beneytout et. al. reported that, the steroid of *Dioscorea*, diosgenin, induces morphological and biochemical changes characteristic of megakaryocyte cells when diosgenin is added to human erythroleukemia (HEL) cell cultures, and thus, diosgenin can be used as a megakaryocytic differentiation inducer of HEL cells. In Life Sciences, 59(11): 147–57, 1996, a steroid extract of *Dioscorea* was indicated to possess significant activities as an antioxidant to modify serum lipid levels. In Planta Medica. (3):168–71, 1986, the effect of glycans of *Dioscorea* on hypoglycemic activity in normal and alloxan-induced hypoglycemic mice have been discussed.

In recent years, people make many efforts to study the medicinal effect of *Dioscorea* polysaccharide. In Journal of China Pharmaceutical University, 25(6):369–72, 1994, it was reported that *Dioscorea* polysaccharide decreased, in vitro, the NADPH-Vc induced and cysteine-$Fe^{2+}$ induced Malondialdehyde formation of brain, liver and kidney microsome in rats, and scavenged superoxide radicals generated by hypoxanthine/xanthine oxidase reaction system and Fenton reaction system. Therefore, *Dioscorea* polysaccharide seems to be used as an antioxdant and superoxide radical scavenger.

In Journal of Plant Resources and Environment, 5(2):5–8, 1996, it illustrated that the content of polysaccharide and allantoin of *Dioscorea* tuber have remarkable effect on lowering the sugar and lipid levels in blood.

In HENAN TCM, 16(6):349–350, 1996, the effect of polysaccharide extract of *Dioscorea* sp. on immunological function was studied, wherein the polysaccharide extract was stated to be prepared by following steps: alcohol reflux, heat extraction with water, concentration, deproteinization by trichloroacetic acid, precipitation by adding 8×, 95% alcohol, dissolution in water, dialysis and dryness. From the given Examples and data, it is showed that the obtained polysaccharide can improve the phagocytosis of macrophage, hemolysin formation, lymphocyte conversion and enhance T cell percent in peripheral blood.

Other studies concerning water extract of *Dioscorea*, prepared by water extraction and alcohol precipitation, can be found in HENAN TCM, 12(1):23–24, 1992. In that article, the water extract was indicated to be able to improve the hemolysin formation, lymphocyte conversion and to enhance T cell percent in peripheral blood.

In accordance with this invention, it provides an oral composition comprising a *Dioscorea* polysaccharide extract. The polysaccharide extract is capable of improving the immunological activity by regulating the cytokine gene expression.

Further extensive study showed that *Dioscorea* polysaccharide prepared by the method of this invention remarkably enhances the effect of oral vaccine on systemic and mucosal responses of a subject upon vaccination with an oral vaccine. More specifically, *Dioscorea* polysaccharide has an effect on induction of the systemic IgG and mucosal IgA antibodies specific to the oral vaccine. This synergistic effect of *Dioscorea* polysaccharide on immunization with an oral vaccine is neither disclosed nor suggested in the prior art.

SUMMARY OF THE INVENTION

It is an object of this invention to provide an oral composition, comprising a polysaccharide extract of *Dioscorea* sp. prepared by a process comprising the steps of:

(1) using an alcohol based solvent in the presence of an acid to extract a tuber of *Dioscorea* sp. to obtain an insoluble solid portion;

(2) subjecting the insoluble solid portion to an aqueous solvent in the presence of a starch hydrolyzing enzyme to obtain an aqueous solution; and (3) subjecting the aqueous solution to an alcohol based solvent so that a polysaccharide extract of *Dioscorea* sp. is precipitated and collected from the aqueous solution.

It is another object of this invention to provide an oral composition comprising a polysaccharide extract prepared from *Dioscorea* sp., which can be used to enhance the immunological activity by induction of cytokine gene expression in lamina propria and Peyer's patch of the subject, wherein the cytokine is selected from the group consisting of IL-2, IFN-$\gamma$, IL-4, IL-5, IL-6, IL-10, and TGF-$\beta$.

It is still another object of this invention to provide an oral composition comprising a polysaccharide extract prepared from *Dioscorea* sp., which can be used to enhance the effect of an oral vaccine on systemic and mucosal responses via oral route, and exhibits a synergistic effect if administered with an oral vaccine.

BRIEF DESCRIPTION OF THE DRAWINGS

The above and other objects and features of the present invention will become apparent with reference to the following description of the preferred embodiments taken in conjunction with the accompanying drawings, in which.

DETAILED DESCRIPTION OF THE INVENTION

In accordance with the present invention, a process for preparing a target polysaccharide extract of *Dioscorea* sp. comprising:

(1) using an alcohol based solvent in the presence of an acid to extract a tuber of *Dioscorea* sp. to obtain an insoluble solid portion;

(2) subjecting the insoluble solid portion to an aqueous solvent in the presence of a starch hydrolyzing enzyme to obtain an aqueous solution; and (3) subjecting the aqueous solution to an alcohol based solvent so that a polysaccharide extract of *Dioscorea* sp. is precipitated and collected from the aqueous solution.

Preferably, the alcohol based solvent used in steps (1) and (3) of the process is selected from the group consisting of methanol and ethanol based solvent, and the acid used in step (1) is 1% acetic acid.

Further, the starch hydrolyzing enzyme used in step (2) of the process is α-amylase, preferably is 0.6% by weight of α-amylase. The step (2) can be carried out at an elevated temperature, preferably at 80° C.

In the present invention, the preparing process further comprises a step of treating the polysaccharide extract with a deproteinizing agent so as to remove proteineous portions therefrom. The deproteinizing agent is a solvent mixture capable of removing protein from the polysaccharide extract. One example of the solvent mixture in the preferred embodiment is a mixture of chloroform and 1-butanol.

In the past, many studies have indicated the improved effect of *Dioscorea* polysaccharides on immunological activity. However, it has yet to be investigated as to how the *Dioscorea* polysaccharide-based medicinal product regulates immunological activity at the molecular level, which is to understanding of its pharmaceutical mechanism underlying such immunological activity, and hence, its applications in medical treatments.

In mucosal immunity, especially in antibody response, CD4 T cells induce B cells to express and secret IgA by directly contacting B cell with $T_H2$ cell and producing signal from cytokines. Naive CD4 T cells can differentiate upon activation into either TH1 or $T_H2$ cells, which differ in the cytokines they produce and in their function. $T_H1$ cells secret IL-2 and IFN-γ, which activate macrophages; $T_H2$ cells secret IL-4, IL-5, IL-6, and IL-10, all of which activate B cells. In addition, in mucosal immunity, there exists unique cells, $T_H3$ cells, which produce mainly TGF-β in response to antigen, induce B cells to secret IgA, and stimulate isotype conversion into IgA.

To further confirm whether the effect of *Dioscorea* polysaccharides on immunological activity is through the regulation of cytokine gene expression, the inventor investigated the effect of *Dioscorea* polysaccharides on gene expression of cytokines, particularly IL-2, IFN-γ, IL-4, IL-5, IL-6, IL-10, and TGF-β. The results are shown in FIG. 1–2.

Figure 1:
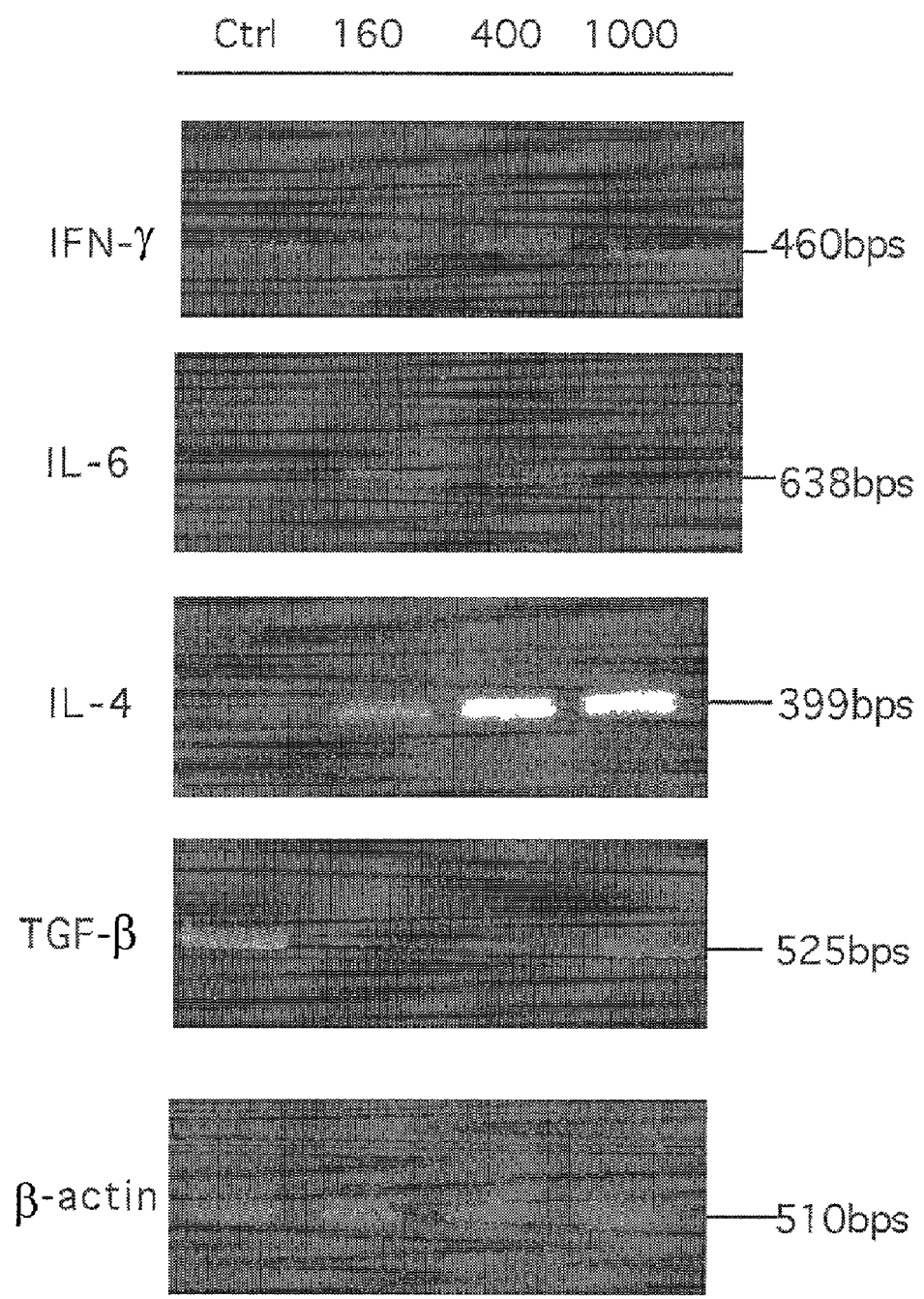
FIG. 1 is a photograph showing the RT-PCR result of cytokines in Peyer's patch isolated from mice which orally administered with the *Dioscorea* polysaccharides according to the present invention.
Figure 2:
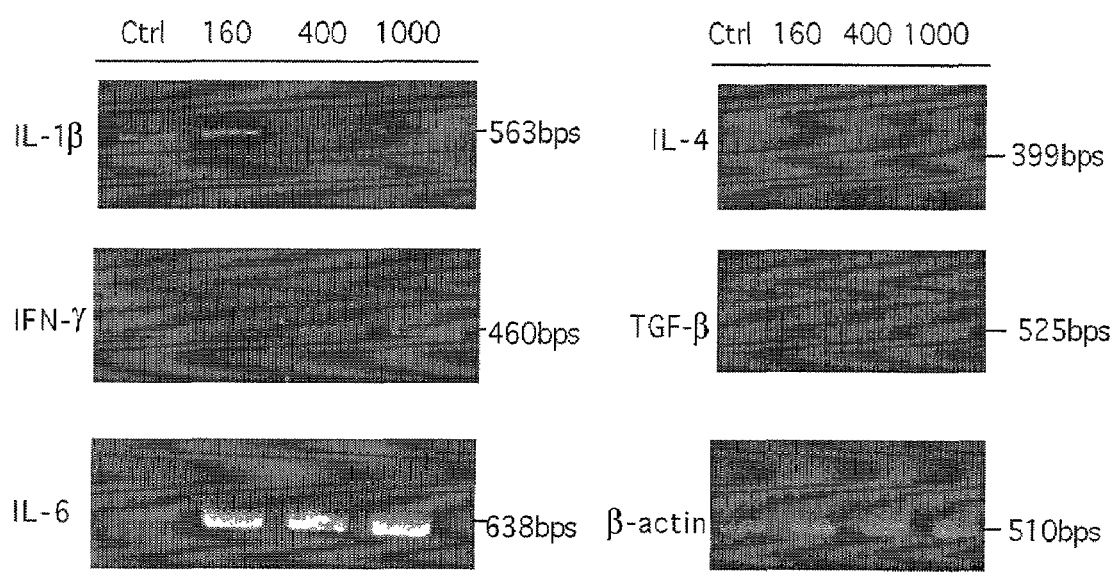
FIG. 2 is a photograph showing the RT-PCR result of cytokines in lamina propria isolated from mice which orally administered with the *Dioscorea* polysaccharides according to the present invention.

In the experimental results shown in FIGS. 1–2, the gene expressions of IFN-γ, IL-4 and IL-6 in Peyer's patch are increased, especially IL-4. In lamina propria, the gene expression of IFN-γ, IL-4, IL-6 and TGF-β are increased, especially IL-6. The results suggest that the polysaccharide extract prepared from *Dioscorea* sp. may activate macrophages and make the surface cell in lumen of intestine become a better antigen presenting cells by increasing IFN-γ expression in lamina propria; may stimulate B cells activation and increase the secretion of antibodies by increasing the gene expression of IL-4 and IL-6; and stimulate the conversion of IgM into IgA by increasing the gene expression of TGF-β in lamina propria. In view of above, the *Dioscorea* polysaccharide extract prepared by the method of this invention may modulate the immunological response by regulating the cytokine expression.

In addition, the applicant unexpectedly found that the oral composition comprising the *Dioscorea* polysaccharide extract prepared by the method of this invention can be used to enhance the immunological effects of an oral vaccine administered to a subject in need thereof.

The majority of vaccines are given by injection. This route is disadvantageous in either of the practical and immunological aspects. Injections which require needles, syringes and a trained injector, are painful and more expensive, and thus unpopular with recipient. In view of limited dosage of each uptake via the route of injection, mass vaccination by the injection is quite laborious. The immunological drawback with the injection is that the route of injection is not the usual one of entry of the majority of pathogens against which the vaccination is directed.

Many pathogens initially invade the host via the mucosal surfaces. The mucosal surfaces of the gastrointestinal, respiratory and urogenital tracts have a common mucosal immune system which is fully equipped with immune cells. At several sites in the mucosal lining, organized accumulations of lymphoid and non-lymphoid cells are situated directly underneath the epithelium. These accumulations together form the mucosa-associated lymphoid tissues (MALT). Antigens which are inhaled or ingested enter lymphoid tissue via specialized antigen sampling cells, M cells, which occur in the epithelium of MALT, and induce B and T cell responses. In these tissues, differentiation of immunoglobulin $M^+$ ($IgM^+$) B cells to $IgA^+$ B cells occurs, regulated by T cells and cytokines. The IgA+ B cells migrate to local lymph nodes and enter into the systemic circulation. IgA+ plasma cells selectively home to the mucosal sites where the antigen was first encountered, and can also home to distant mucosal sites where synthesis and secretion of IgA then occur.

The immunological reactivity at mucosal surface is partly characterized by having predominantly microbe-specific secretory IgA (S-IgA) antibodies as the major humoral defence factor. Secretory IgA antibodies inhibit microbial adherence and prevent absorption of antigens from mucosal surfaces.

Compared with the systemic immune system, the mucosal immune system matures more rapidly. Further, mucosal immunization has been shown to induce both antigen-specific S-IgA and IgG responses in secretions and serum, respectively. Thus, mucosal immunization may be more efficacious than systemic vaccination, since the latter route of immunization induces only systemic but not mucosal immune responses.

According to the previous considerations, oral vaccines are more desirable due to their ease of administration and their higher acceptability of patients. Another advantage is that oral vaccines may stimulate production of mucosal antibodies more effectively than injected vaccines. This is important as the mucosal immune system is a first line of defense against many pathogenic organisms, and matures more rapidly as described above.

However, oral administration of antigen suffers from two difficulties, one is poor immunogenicity if the antigen is T cell-independent (i.e. polysaccharide antigen) and the other is oral tolerance if the antigen is T cell-dependent (i.e. protein antigen).

First, concerning the poor immunogenicity, polysaccharide vaccines, such as Pneumococcus vaccine including 23 of the most prevalent serotypes, are efficacious in healthy adults, but elderly and patients with immunodeficiencies respond poorly to the capsular polysaccharide (PPS) and consequently account for most of the invasive infectious diseases. The limitations of such vaccines are thought to be due to the thymus-independent type 2 (TI-2) character of the PPS antigens. Characteristics of a TI-2 type immune response include late development in ontogency, no memory response, and isotype restriction.

To overcome such poor immunogenicity, vaccines were conjugated with a protein complex, such as the outer membrane protein complex of Neissera meningitides (OMPC), however, no local secretory IgA anti-polysaccharide response was detected. In Vaccine 14(5): 392–398, 1996, J. L. VanCott et. al., it was taught that, oral immunization with pneumococcal polysaccharide (Pnup) in the presence of mucosal adjuvant, such as cholera toxin, could induce Pnup-specific IgA responses whereas Pnup alone did not.

Second, oral administration of antigen may, in some case, lead to immunologic unresponsiveness, a condition termed "oral tolerance." Therefore, different oral adjuvant, vector and immunomodulator as well as cytokines are being investigated for their ability to induce well-defined immune responses.

In the present invention, the *Dioscorea* polysaccharide extract is studied to evaluate the effect of oral *Dioscorea* polysaccharide extract on mucosal and systemic responses induced by oral bacterial polysaccharide and the effect of oral *Dioscorea* polysaccharide extract on inhibition of oral tolerance induced by extrinsic protein.

From the experimental results of FIGS. 3–7, the applicant unexpectedly found that the effect of orally administered *Dioscorea* polysaccharides extract, which is prepared by the method of this invention, on mucosal (intestinal and pulmonary) IgA level and serum IgG level induced by orally immunizing with Pneumovax 23 was evidently enhanced. This result illustrates that the *Dioscorea* polysaccharide extract can enhance the immunological effects of an oral vaccine administered to a subject in need thereof and have a synergistic effect with the oral vaccine, and is capable of enhancing the IgA level so as to improve the first line of defense against a wide variety of pathogens. The polysaccharide extract also might offer a more efficacious vaccination for the elderly or patients with immunodeficiencies and is safer than the used cholera toxin.

To study the effect of *Dioscorea* polysaccharide extract on inhibition of oral tolerance, this invention use Ovalbumin as an extrinsic protein. In FIGS. 8–11, the data shows that the *Dioscorea* polysaccharides extract can increase the mucosal (intestinal and pulmonary) IgA level and serum IgM and IgG level induced by orally immunizing with Ovalbumin in C57BL/6 and C3H mice. The result clearly illustrates that *Dioscorea* polysaccharide extract can inhibit the oral tolerance caused by extrinsic protein.

The experiments performed in accordance with the present invention clearly demonstrate that *Dioscorea* polysaccharides extract is orally active in immunomodulating effect, enhancement of mucosal and systemic immunities and elimination of oral tolerance. The present invention therefore provides an application of *Dioscorea* polysaccharides with oral vaccine in microbial infecting disease.

EXAMPLES OF THE INVENTION

The following Examples are given for the purpose of illustration only and are not intended to limit the scope of the present invention.

Example 1

Extraction and Isolation of Polysaccharides Extract from *Dioscorea* sp.

4 kg Peeled tubers of *Dioscorea* sp. harvested from Yang-Ming Mountain in Taiwan were immersed in methanol solution in the presence of 1% acetic acid. After stirring and adjusting the concentration of methanol to 40% by volume, the mixture solution was allowed to stand overnight, and then separated by centrifugation. The precipitate was lyophilized and powdered, and then, added in water and held at 80° C., in the presence of 0.6% α-amylase to decompose starch. A supernatant solution was obtained by centrifugation, and treated with a 75% alcohol solution for several times to obtain a precipitated solid portion. The obtained precipitated solid portion was then treated with a chloroform/1-butanol (1/3) de-proteinizing process. Thereafter, the polysaccharide extract was precipitated by using 75% alcohol solution. The orally active polysaccharide extract was obtained therefrom by lyophilizing the re-dissolved polysaccharide-containing solution.

Example 2

Reverse Transcription and Polymerase Chain Reaction of Cytokines Isolation of Peyer's Patch Cells

*Dioscorea* polysaccharide extract was administered orally by food-intake (0, 160, 400, 1000 mg/Kg) for 3 days to mice.

The mice were then sacrificed and small intestine was obtained. The obtained small intestine was placed in a dish containing 1×HBSS solution and Peyer's patch was cut off. Peyer's patch was torn into small pieces by needles and tweezers, the cells was obtained by filtration with No. 53 mesh and centrifugation, and cells (about 1–2×10$^7$) were resuspended for RNA isolation.

Isolation of Lamina Propria Cells

The intestinal fragments from which the epithelium cells has been removed were placed in 10–15 ml complete medium containing RPMI, Hepes, 2-ME and FCS so as to terminate the reaction of EDTA and DTT. The fragments were incubated in 40 ml complete medium with 30 units Collagenase I and 10 units Collagenase II at 37° C. for 60 minutes. The cells were filtered by glass wool and No. 53 mesh, followed by centrifugation at 1000 rpm for 5 minutes.

blastosis virus) reverse transcriptase and the buffer thereof, and the final reaction volume was 26.5 μl. cDNA was obtained by reacted previous reaction solution at 42° C. for 60 minutes and then at 90° C. for 5 minutes. 2.5 μl resultant cDNA was added with 0.5μl 10 mM dNTP, 0.5 μl polymerase (2 units) and the buffer thereof, 1μl of 10 μM targeted primers, and the final volume of the reaction mixture was 25 μl. PCR was performed for 30 cycles, each cycle consisting of 45 seconds of denaturation at 94° C., 45 seconds of annealing at 63° C. and 1 min of extension at 72° C. The reaction products were visualized by electrophoresis in 2% agarose gel. Sequences of the PCR primers were shown in Table 1. The experimental results were shown in FIGS. 1–2.

In FIGS. 1–2, the gene expressions of IFN-γ, IL-4 and IL-6 in Peyer's patch are increased, especially IL-4; and in lamina propria, the gene expression of IFN-γ, IL-4, IL-6 and TGF-β are increased, especially IL-6.

TABLE 1

Sequences of the primers used in RT-PCR

| Cytokine | Sequence (5' to 3') | Size (bp) | SEQ ID NO |
|---|---|---|---|
| IL-1β | | | |
| upstream | ATG GAC ACT GTT CCT GAA CTC AAC T | | 1 |
| downstream | CAG GAC AGG TAT AGA TTC TTT CCT TT | 563 | 2 |
| IL-4 | | | |
| upstream | ATG GGT CTC AAC CCC CAG CTA GT | | 3 |
| downstream | GCT CTT TAG GCT TTC CAG GAA GTC | 399 | 4 |
| IL-6 | | | |
| upstream | ATG AAG TTC CTC TCT GCA AGA GAC | | 5 |
| downstream | CAC TAG GTT TGC CGA GTA GAT CTC | 638 | 6 |
| IFN-γ | | | |
| upstream | TGA ACG CTA CAC ACT GCA TCT TGG | | 7 |
| downstream | CGA CTC CTT TTC CGC TTC CTG AG | 460 | 8 |
| TGF-β | | | |
| upstream | TGG ACC GCA ACA ACG CCA TCT ATG CCA TCT ATG AGA AAA CC | | 9 |
| downstream | TGG AGC TGA AGC AAT AGT TGG TAT CCA GGG CT | 525 | 10 |
| β-actin | | | |
| upstream | GAC TAC CTC ATG AAG ATC CT | | 11 |
| downstream | CCA CAT CTG CTG GAA GGT GG | 510 | 12 |

The cells pellet was washed with 1×HBSS, and centrifuged with 70% Percoll and 42% Percoll (5 ml) at 2000 rpm for 20 minutes. The live cells at middle layer were obtained, washed with 10 ml 1×HBSS, centrifuged and resuspended at the concentration of 1–3×10$^6$ cells/ml for RNA isolation.

Reverse Transcription and Polymerase Chain Reaction of Cytokines

Total RNA was extracted from Peyer's patch cells and lamina propria cells by using Ultraspec™ RNA isolation kit (Biotex laboratories INC, U.S.A.). 5 μg total RNA and 2.5 μg oligo dT were heated at 70° C. for 10 minutes, cooled to room temperature for 10 minutes, added with 4 μl 10 mM dNTP, 0.5 μl rRNasin, 1μl (10 units) AMV (Avian Myelo- Example 3

Enhancement of Antibody Response to Bacterial Polysaccharide Antigen and Ovalbumin by Oral Intake of *Dioscorea* Polysaccharide Vaccination (1) Oral Vaccination with Pneumovax 23

C57B/6j mice at 10 and 20 weeks of age were used for this study and kept in a specific pathogen free environment in the Animal Center of National Yang-Ming University, Taiwan. For long-term administration of *Dioscorea* polysaccharide, three days prior to inoculation, experimental groups (3 mice/group) were supplemented with *Dioscorea* polysaccharide at the doses of 10, 50, 250 mg/kg/day in daily drink until the mice were sacrificed. On the other hand, for short-term administration of *Dioscorea* polysaccharide, *Dioscorea* polysaccharide at the doses of 10, 50, 250 mg/kg/day in daily drink was merely supplemented at days 0, 1, 7 and 8, and the oral inoculation was carried out at days 1 and 8. Pre-immune serum was obtained from eyes before supplementation with *Dioscorea* polysaccharide. Oral inoculation was carried out by administration of a dose of 25 μg of Pneumovax 23 (Merck & Co., Inc. West point, Pa., USA) after neutralizing the gastric acid with 1.5% sodium bicarbonate in 1×HBSS. The serum samples were collected from eyes on days 7, 14 and 21 after inoculation and the mice were sacrificed at day 15 after oral inoculation and the intestinal tract and lung were obtained and flushed.

(2) Oral Adminstration with Ovalbumin

C57B/6j and C3H mice at 20 weeks of age were used for this study and kept in a specific pathogen free environment in the Animal Center of National Yang-Ming University in Taiwan. Three day prior to immunization, experimental groups (3 mice/group) were supplemented with *Dioscorea* polysaccharide at the doses of 10 and 50 mg/kg/day in daily drink until the mice were sacrificed. Pre-immune serum was obtained from eyes before supplementation with *Dioscorea* polysaccharide. Oral immunization was carried out by administration of 20 mg Ovalbumin in 500 μl of PBS at day 1, 8 and 29. The serum samples were collected from eyes on day 36 after immunization and the intestinal tract and lung were obtained and flushed.

Collection of the Flushing Solution from Intestinal Tract and Lung of Mice (1) Collection of the Flushing Solution from Intestinal Tract of Mice The intestine between the rectum and the end of the small intestine was obtained and placed in 6 ml enzyme inhibitor solution (0.01% soybean trypsin inhibitor in 50 mM EDTA). The intestine was cut longitudinally and washed with enzyme inhibitor solution. The washing solution was placed in 50 ml tube and the tissue pieces were dispersed and shaken to make sure that the solution was homogeneous. The solution was centrifuged at 650 g for 10 minutes to obtain the supernatant. 30 μl 100 mM PMSF in 95% alcohol was added into the supernatant, the mixture solution was centrifuged to obtain the supernatant. 20 μl PMSF and 20 μl sodium azide (1% w/v) were added into the supernatant and the solution were stood on ice for 15 minutes and added with 100 μl FCS, mixed and stood at −20° C.

(2) Collection of the Flushing Solution from Lung of Mice

The trachea of mice was flushed back and forth 5 times with 1 ml 1% BSA solution by 1 ml syringe with a hose and all flushing solution were collected and centrifuged at 8500 rpm for 10 minutes. The supernatant was collected and stored at −20° C. for ready to use.

Antibodies Analysis by ELISA 96-well microtiter plates were precoated with 50 μl Pneumovax 23 (1 μl of Pneumovax 23 vaccine in 49 μl of PBS) or 100 μl Ovalbumin solution (4 μg/ml in 50 mM sodium carbonate/bicarbonate buffer, pH 9.6) at 4° C. overnight. After washing three times with washing solution (Tween 20 in PBS, 0.05% v/v), 200 μl PBS-BSA(1% BSA in PBS, w/v) was added into wells and incubated at room temperature for 1 hour. After washing three times with washing solution, 100 μl tested plasma (diluted 100× with PBS-BSA), intestinal flushing solution or pulmonary flushing solution were added into wells and reacted at room temperature for 2 hours. Wells were then washed six times with 200 μl PBS containing 0.05% Tween 20, added with 100 μl secondary antibody (goat-anti-mouse IgG or IgA or IgM conjugated with alkaline phosphatase) diluted 1000× with PBS-BSA, and stood at room temperature for 2 hours. Wells were then washed six times with 200 μl washing solution (Tween 20 in PBS, 0.05% v/v), followed by rinsing with 100 μl reaction buffer solution (diethaloamin buffer: 9.7% v/v diethaloamin and 0.01% v/v magnesium chloride, pH=9.8) and added with 100 μl reactant (p-nitrophenyl phosphate, 1 mg/ml in diethaloamin buffer) for color development. The reaction solution was reacted at room temperature for 10–20 minutes. Titers were then recorded by ELISA reader at an absorbance of 410 nm.

Figure 3:
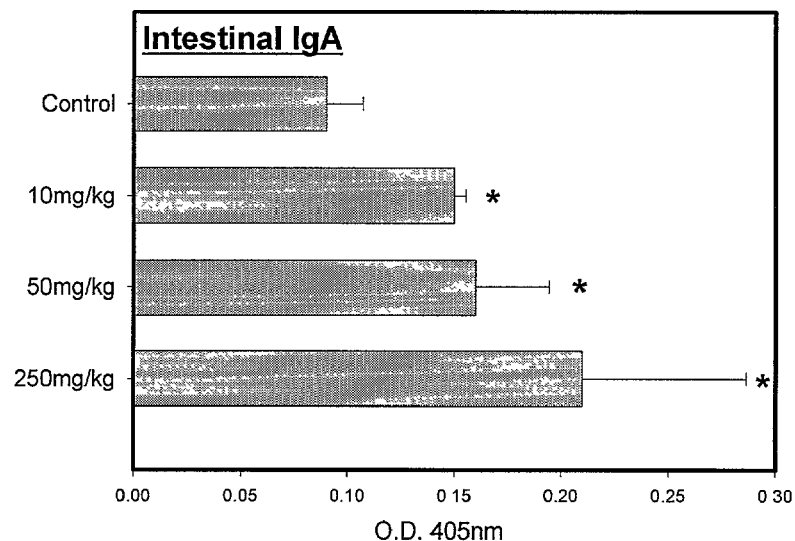
FIG. 3 is bar graph illustrating the Pneumovax 23 vaccine-specific IgA responses in (A) intestinal lavage and (B) pulmonary lavage of 20 weeks C57BL/6, which are induced by oral *Dioscorea* polysaccharide of this invention.
Figure 3:
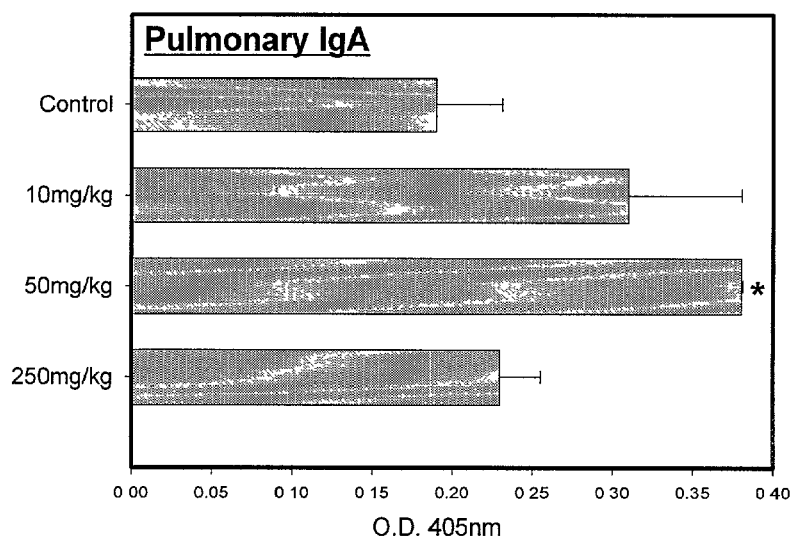
Figure 4:
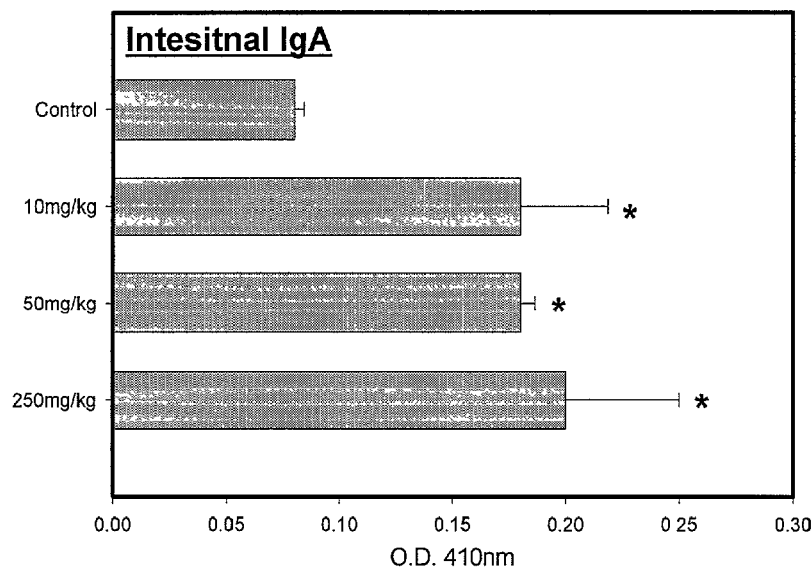
FIGS. 4 and 5 are bar graphs illustrating the Pneumovax 23 vaccine-specific IgA responses in (A) intestinal lavage and (B) pulmonary lavage of 10 weeks C57BL/6, which are induced by oral *Dioscorea* polysaccharide of this invention.
Figure 4:
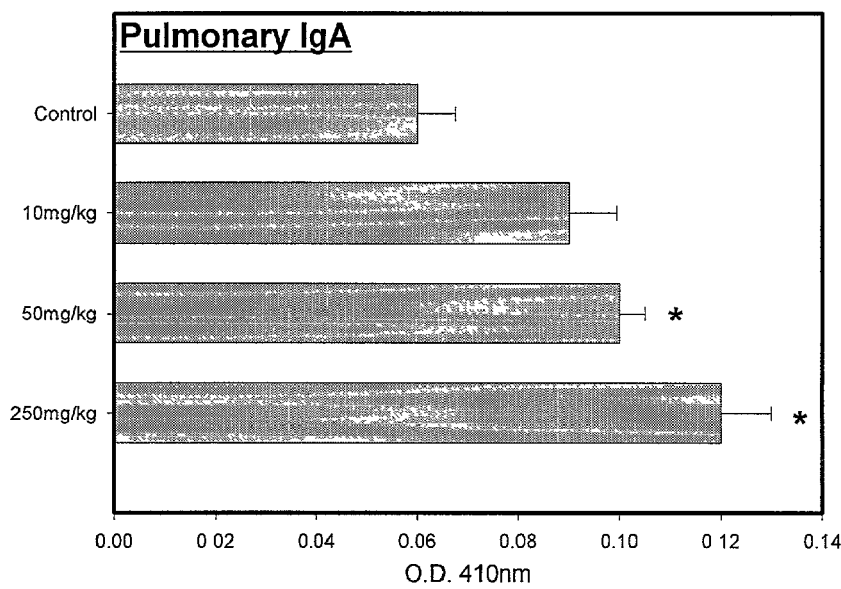
Figure 5:
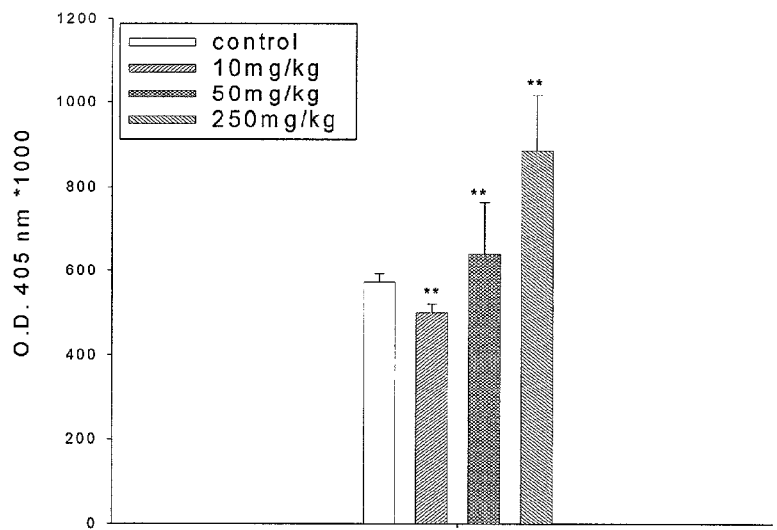
Figure 5:
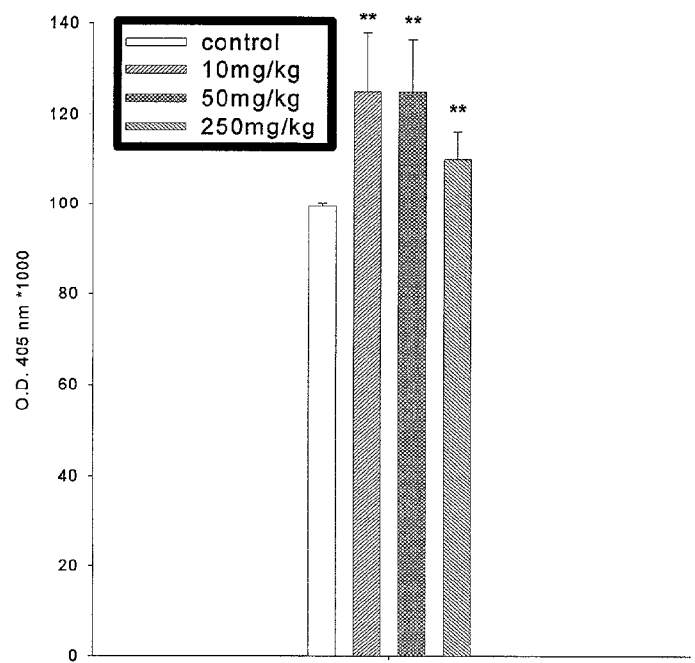

As shown in FIGS. 3–5, IgA titers of the 10 and 20 weeks C57BL/6 mice orally immunized with Pneumovax 23 vaccine were significantly elevated by the orally active *Dioscorea* polysaccharide extract at the dose of 10–250 mg/Kg for long-term administration (as shown in FIGS. 3A and 4A) and 50–250 mg/Kg for short-term administration (as shown in FIG. 5A) in intestine, and at the dose of 50 mg/Kg for long-term administration (as shown in FIGS. 3B and 4B) and 10–250 mg/Kg for short-term administration (as shown in FIG. 5B) in lung.

Figure 6:
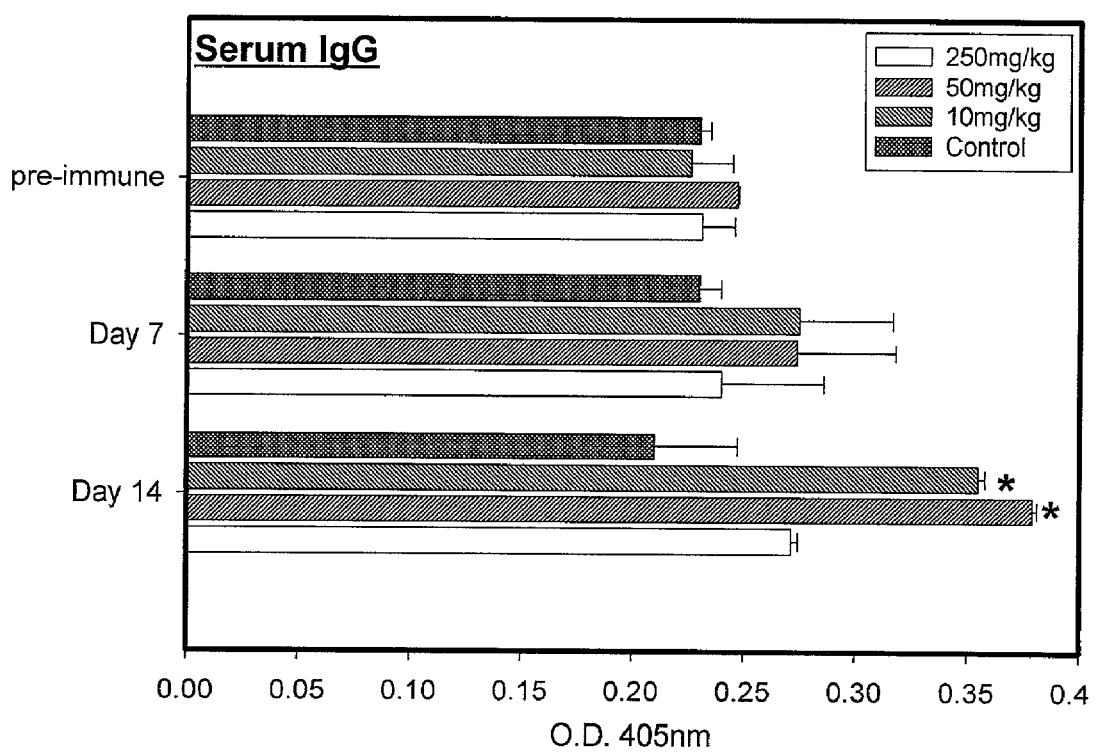
FIGS. 6 and 7 are bar graphs illustrating the Pneumovax 23 vaccine-specific IgG responses in serum, which are induced by oral *Dioscorea* polysaccharide of this invention.
Figure 7:
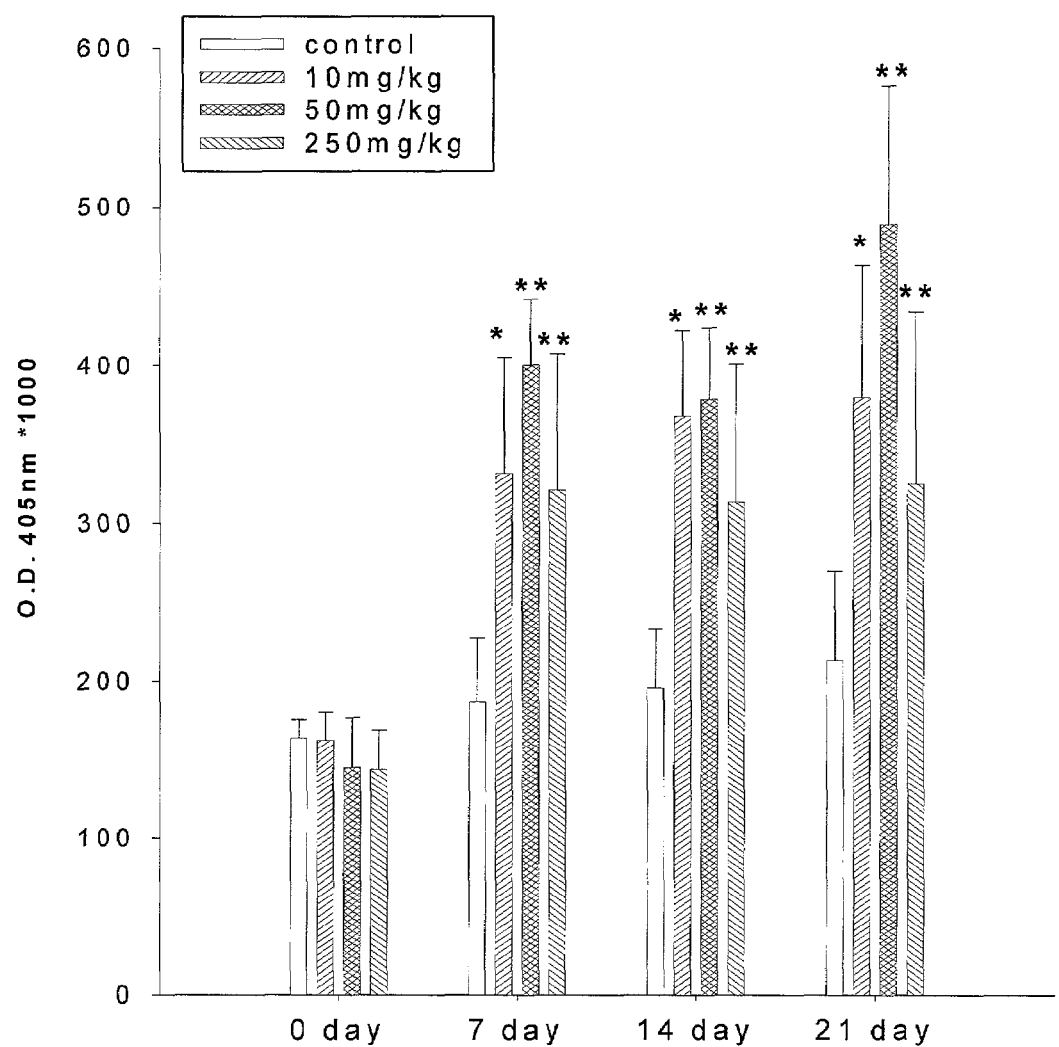
Figure 8:
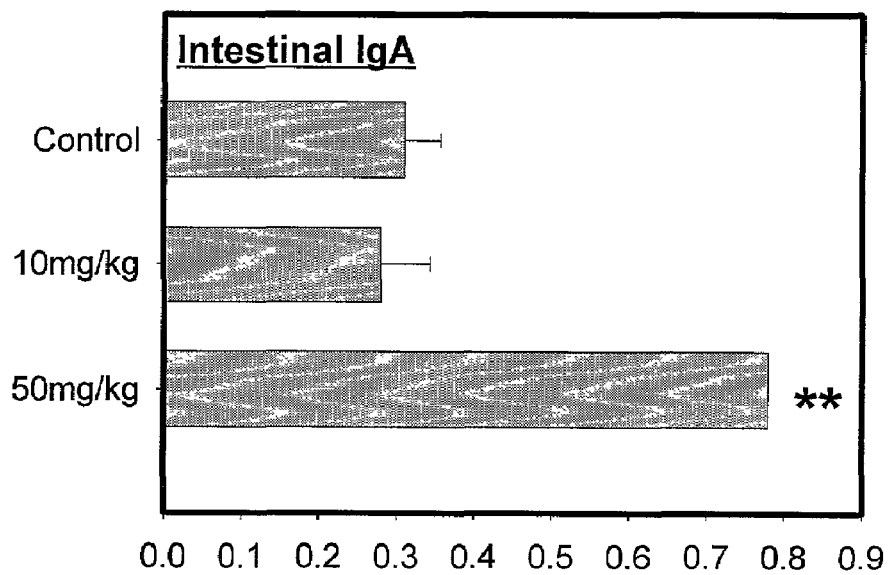
FIGS. 8 and 9 are bar graphs of the IgA responses in (A) intestinal lavage and (B) pulmonary lavage of C57BL/6 mice and C3H mice, which are induced by *Dioscorea* polysaccharide of this invention, to illustrate the ability of *Dioscorea* polysaccharide to inhibit the oral tolerance.
Figure 8:
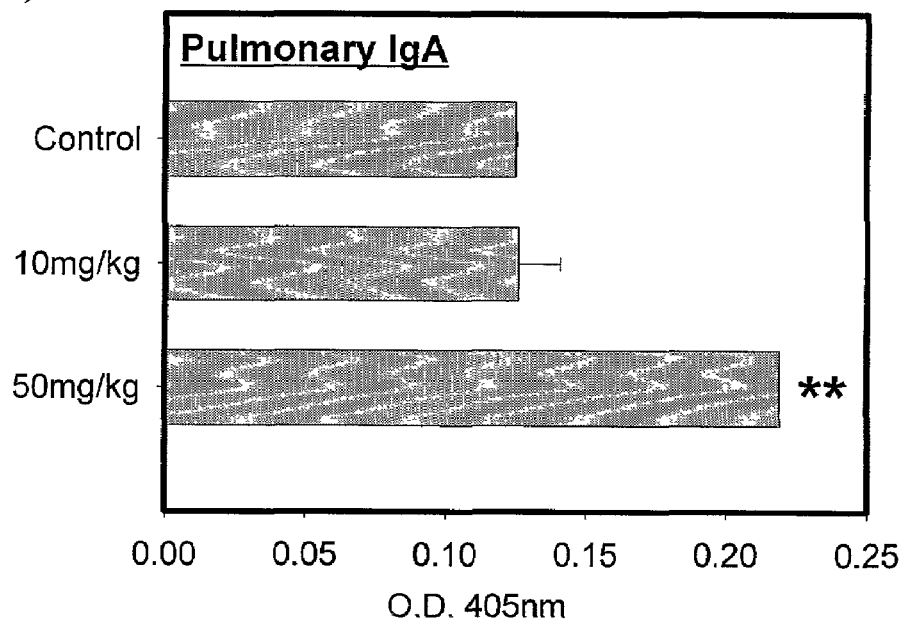
Figure 9:
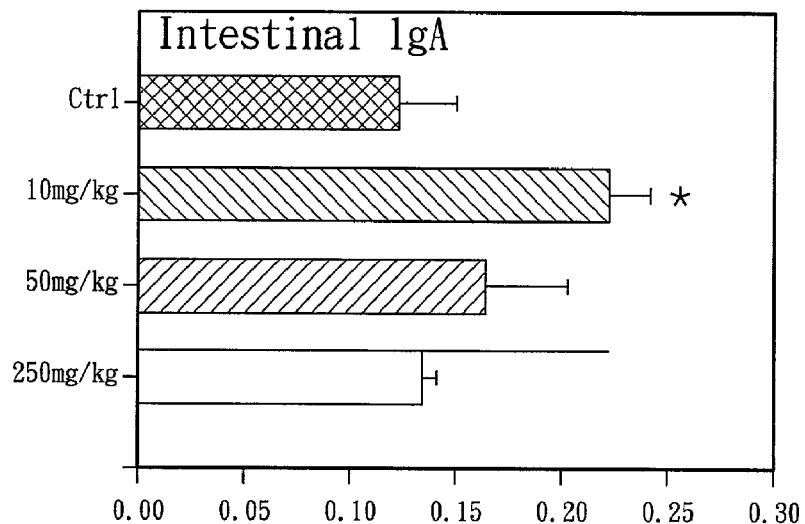
Figure 9:
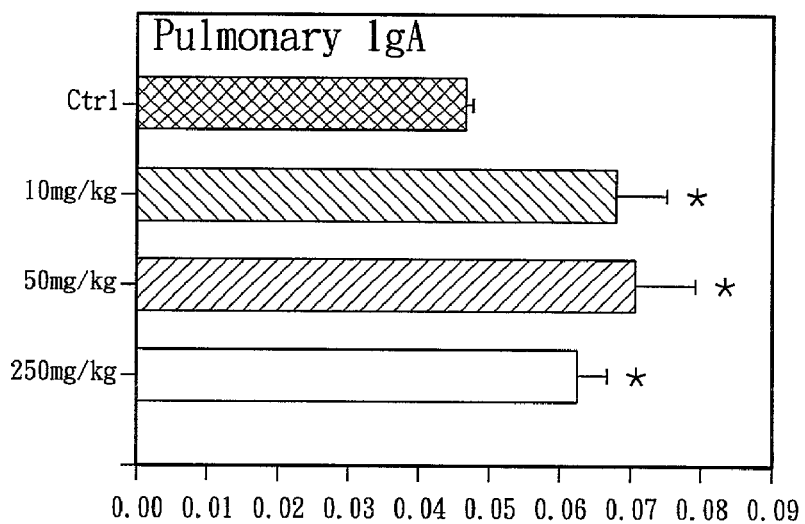
Figure 10:
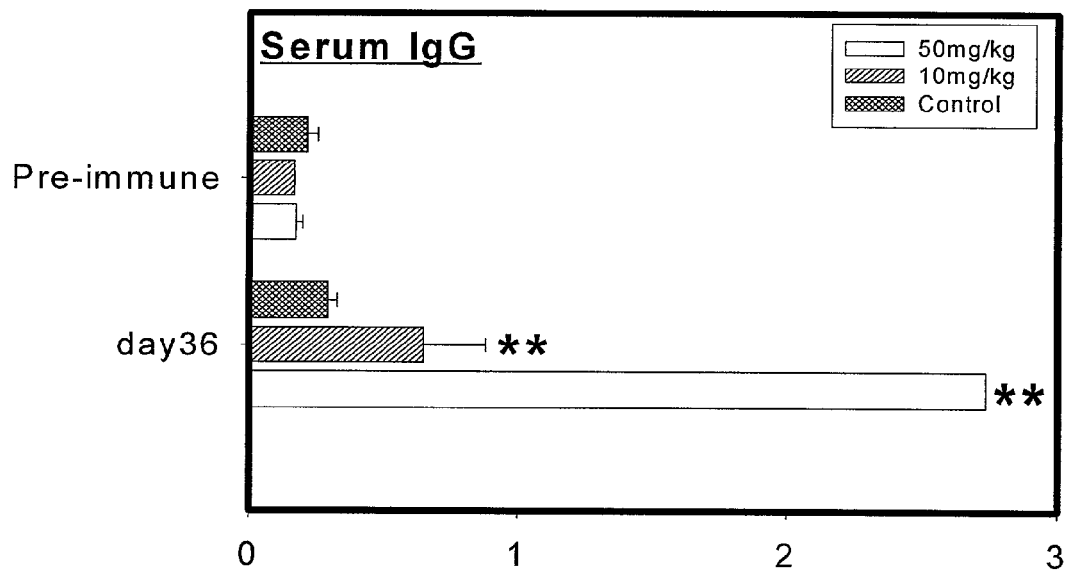
FIGS. 10 and 11 are bar graphs of the (A) IgG and (B) IgM responses in serum of C57BL/6 mice and C3H mice, which are induced by oral *Dioscorea* polysaccharide of this invention, to illustrate the ability of *Dioscorea* polysaccharide to inhibit the oral tolerance.
Figure 10:
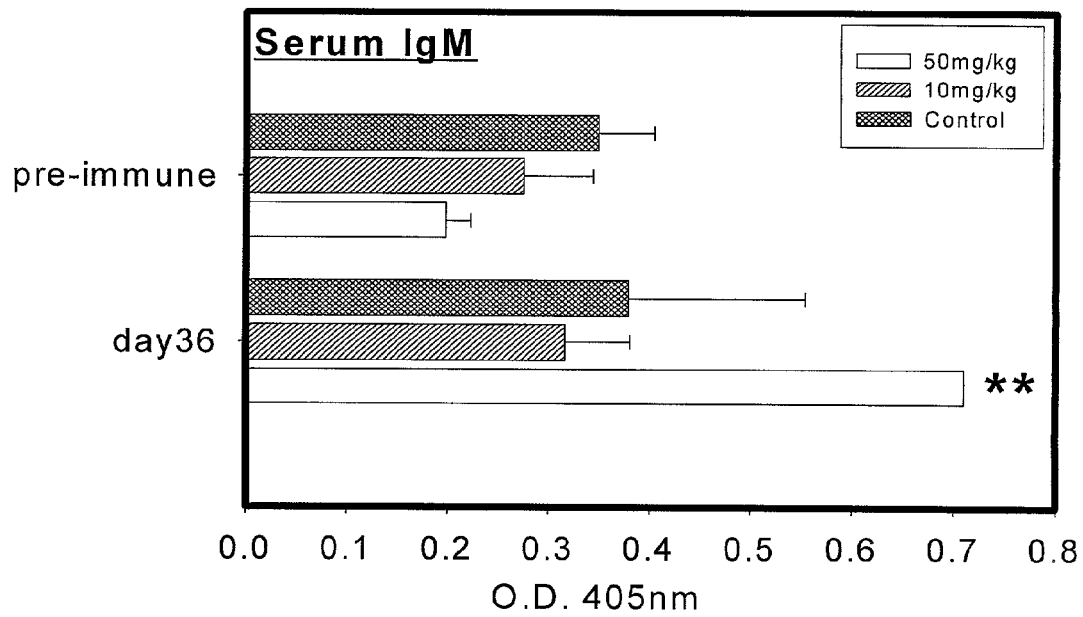
Figure 11:
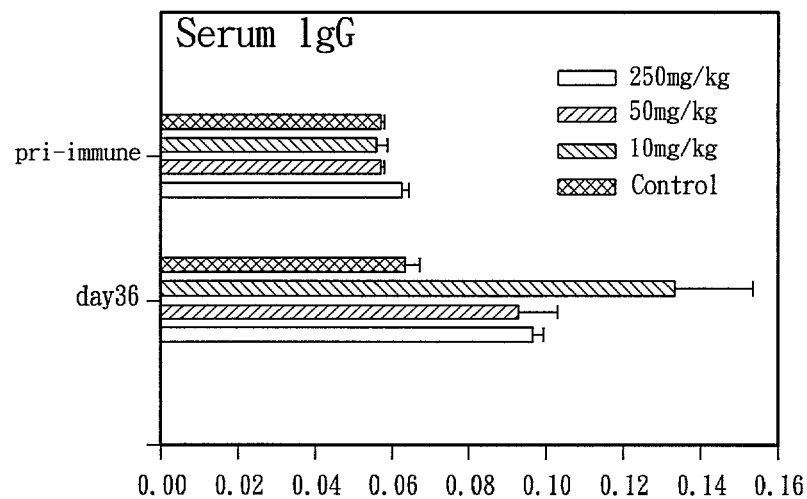
Figure 11:
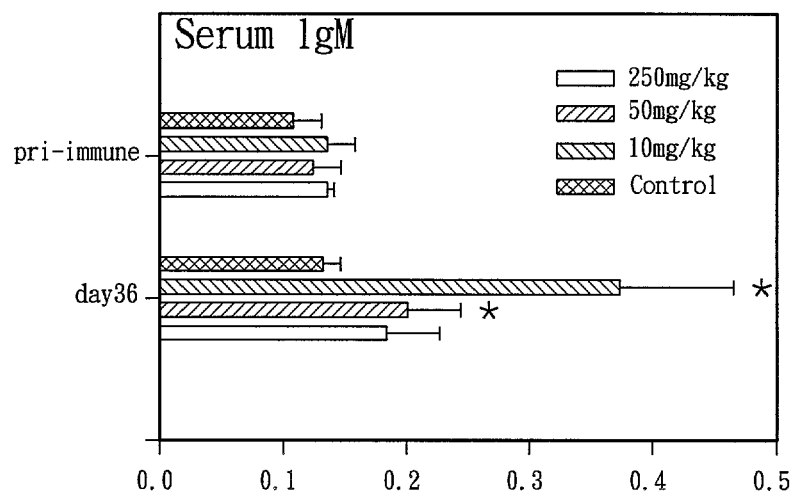

In FIGS. 6 and 7, serum IgG titers of the 10 weeks C57BL/6 mice orally immunized with Pneumovax 23 vaccine were significantly elevated by the orally active *Dioscorea* polysaccharides extract on day 14 at the dose of 10–50 mg/Kg for long-term administration (FIG. 6) and on days 7, 14 and 25 at the dose of 10–250 mg/Kg for short-term administration (FIG. 7).

In FIGS. 8A and 8B, IgA titers in intestine and lung of the 20 weeks C57BL/6 mice orally administered with Ovalbumin were significantly elevated by the orally-active *Dioscorea* polysaccharides extract at the dose of 50 mg/Kg. In FIGS. 9A and 9B, IgA titers of the 20 weeks C3H mice were significantly elevated at the dose of 10 mg/Kg in intestine and at the dose of 10–250 mg/Kg in lung. In FIGS. 10A and 10B, serum IgG titers of the 20 weeks C57BL/6 mice orally administered with Ovalbumin were significantly elevated by the orally active *Dioscorea* polysaccharides extract on day 36 at the dose of 10–50 mg/Kg, and serum IgM titers were elevated on day 36 at the dose of 50 mg/Kg. The elevating phenomenon was also found in 20 weeks C3H mice (see FIGS. 11A and 11B).

While the invention has been described with reference to the above specific embodiments, it should be recognized that various modifications and changes, which will be apparent to those skilled in the relevant art, may be made without departing from the spirit and scope of the invention.

I claim:

1. A process for preparing a polysaccharide extract of *Dioscorea* sp. capable of improving immunological activities in a subject consisting essentially of the steps of:
   (1) extracting a tuber of *Dioscorea* sp. using a 40% methanol solution in the presence of 1% acetic acid, followed by separation, so as to obtain an insoluble solid portion;
   (2) subjecting the insoluble solid portion obtained in step (1) to an aqueous solvent in the presence of a starch hydrolyzing enzyme to obtain an aqueous solution; and
   (3) treating the aqueous solution obtained in step (2) with a 75% alcohol based solvent to obtain a precipitated solid portion; and
   (4) treating the precipitated solid portion obtained in step (3) with a deproteinizing agent to remove proteinaceous substances therefrom.

2. The process according to claim 1, wherein the starch hydrolyzing enzyme used in step (2) is α-amylase.

3. The process according to claim 2, wherein 0.6% by weight of α-amylase is used in step (2).

4. The process according to claim 1, wherein in step (2) the starch hydrolyzing enzyme is α-amylase and is carried out at an elevated temperature of 80° C.

5. The process according to claim 1, wherein the deproteinizing agent used in step (4) is a solvent mixture of chloroform and 1-butanol.

* * * * *